United States Patent

Sugawara et al.

[11] Patent Number: 5,589,517
[45] Date of Patent: Dec. 31, 1996

[54] MODIFIED ION EXCHANGE RESINS AND USE THEREOF

[75] Inventors: Takahiro Sugawara; Michi Watanabe; Naoko Sumitani; Miwa Shirasaki; Toshitaka Suzuki, all of Ami-machi, Japan

[73] Assignee: Mitsubishi Chemical Corporation, Tokyo-to, Japan

[21] Appl. No.: 417,763

[22] Filed: Apr. 6, 1995

[30] Foreign Application Priority Data

| Apr. 8, 1994 | [JP] | Japan | 6-070771 |
| Aug. 11, 1994 | [JP] | Japan | 6-189405 |
| Aug. 19, 1994 | [JP] | Japan | 6-195627 |
| Sep. 5, 1994 | [JP] | Japan | 6-211510 |
| Nov. 9, 1994 | [JP] | Japan | 6-275104 |
| Nov. 9, 1994 | [JP] | Japan | 6-275105 |

[51] Int. Cl.⁶ .............. C07C 39/12; C07C 39/06; C07C 39/16
[52] U.S. Cl. .............. 521/33; 521/32; 525/351; 568/727; 568/728
[58] Field of Search .............. 568/728, 727; 525/351; 521/33, 32

[56] References Cited

U.S. PATENT DOCUMENTS

| 3,394,089 | 7/1968 | McNutt | 568/727 |
| 4,308,405 | 12/1981 | Kwantes | 568/727 |

FOREIGN PATENT DOCUMENTS

| 863390 | 2/1971 | Canada | 568/728 |
| 219432 | 8/1985 | Czechoslovakia . | |
| 0049411 | 4/1982 | European Pat. Off. . | |
| 0144735 | 6/1985 | European Pat. Off. . | |
| 0313165 | 4/1989 | European Pat. Off. . | |
| 0620041 | 10/1994 | European Pat. Off. . | |
| 2685221 | 6/1993 | France . | |

OTHER PUBLICATIONS

European Search Report; Application No. 95105289.3; Dated Jun. 29, 1995.

Primary Examiner—Fred Zitomer
Attorney, Agent, or Firm—Armstrong, Westerman, Hattori, McLeland & Naughton

[57] ABSTRACT

A modified strongly acidic ion exchange resin of a sulfonic acid type is disclosed. Modification is conducted by ionically binding a particular N,N-di-substituted mercaptoalkylamine to a strongly acidic ion exchange resin of a sulfonic acid type. The N,N-di-substituted mercaptoalkylamine is specifically represented by the following formulae:

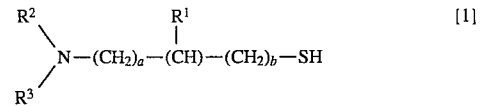

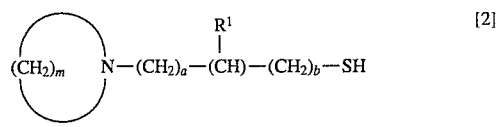

wherein $R^1$ represents hydrogen or a $C_{1-6}$ alkyl group, $R^2$ and $R^3$ independently represent a $C_{1-10}$ alkyl group, a and b denote 0–3, respectively, a+b denotes 2 or 3, and m denotes 4 or 5. The modified ion exchange resin makes an improved catalyst in the preparation of a bisphenol by the condensation reaction of a phenol with a ketone.

8 Claims, 1 Drawing Sheet

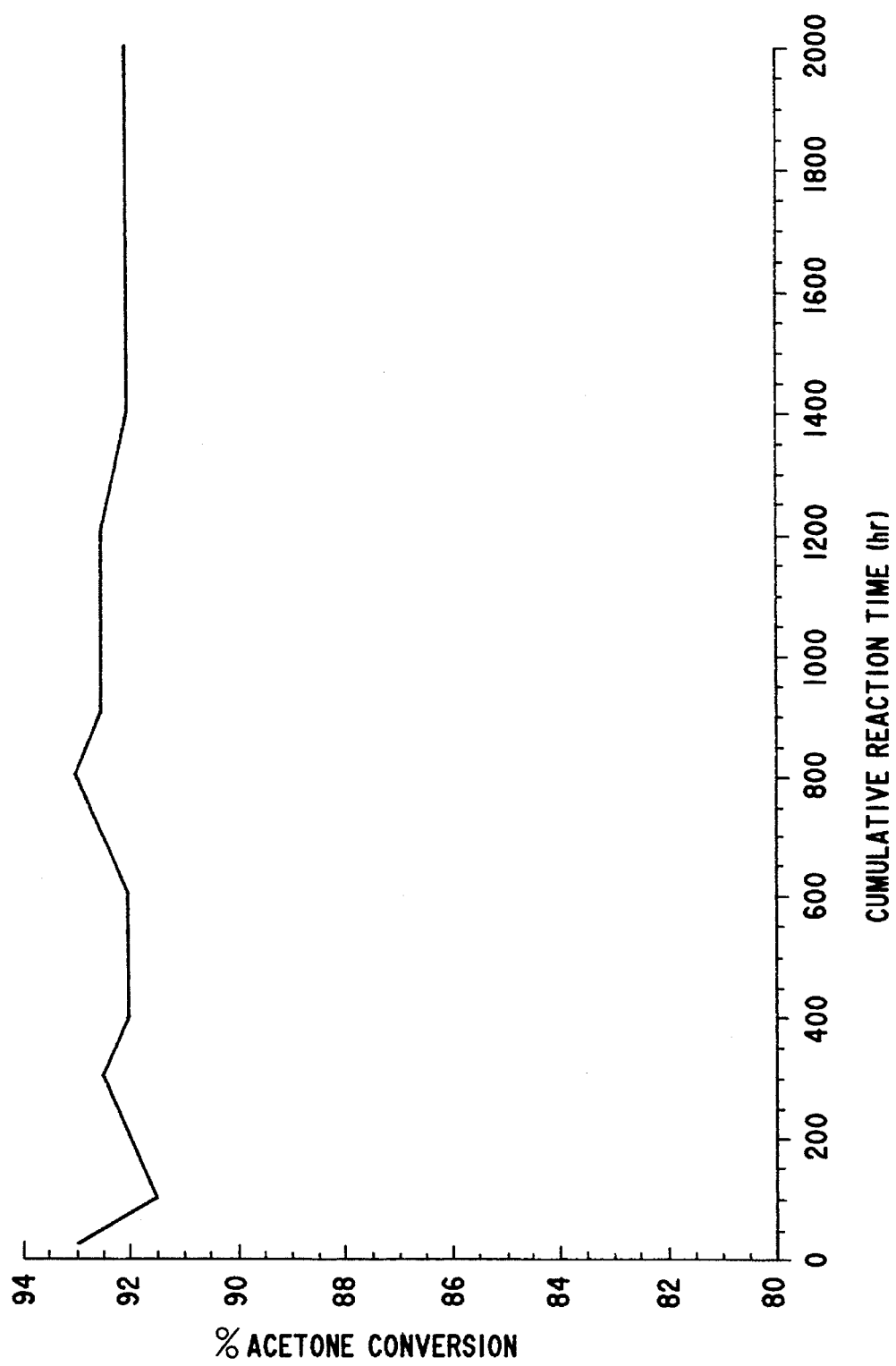

MODIFIED ION EXCHANGE RESINS AND USE THEREOF

FIELD OF THE ART

The present invention relates to a modified strongly acidic ion exchange resin of a sulfonic acid type, where the modification is such that mercapto groups have been introduced thereinto through a unique way. The modified ion exchange resin is useful as a catalyst in the preparation of bisphenols such as bisphenol A by the catalytic condensation reaction of a phenol with a ketone. Bisphenol A is a compound which is useful as a raw material of an epoxy resin or a polycarbonate resin.

RELATED ART

It is known to employ a compound having a mercapto group in combination with a strongly acidic ion exchange resin of a sulfonic acid type as a catalyst in the preparation of a bisphenol, particularly bisphenol A, by the condensation reaction of a phenol with a ketone, particularly phenol and acetone. Specifically, methods where the condensation reaction is carried out in the presence, together with a strongly acidic ion exchange resin, of a compound having a mercapto group as described in Japanese Patent Publication No. 10337/1970 and French Patent No. 1,373,796; where use is made of a strongly acidic ion exchange resin to which a compound having a mercapto group has been covalently linked as described in Japanese Patent Publication No. 14721/1962 and Japanese Patent Laid-Open Publication Nos. 21650/1981, 87846/1982 and 109503/1984; and where use is made of a strongly acidic ion exchange resin to which a mercaptoamine has been ionically linked.

Among these methods, the one where use as the catalyst is made of a strongly acidic ion exchange resin to which a mercaptoamine has been ionically linked may be preferable to the others where use is made of a strongly acidic ion exchange resin to which a compound having a mercapto group has been covalently linked or where use is made of a compound having a mercapto group together with a strongly acidic ion exchange resin in the points of (1) no contamination by a mercapto compound into the product and (2) the preparation of the catalyst with ease.

As the method where use as the catalyst is made of a strongly acidic ion exchange resin to which a mercaptoamine has been ionically linked, known are those where use is made of a strongly acidic ion exchange resin having such an amine ionically linked thereto as 2-mercaptoethylamine as described in Japanese Patent Publication No. 19953/1971 and Japanese Patent Laid-Open Publication No. 298454/1987, N-propyl-3-mercaptopropylamine and N-propyl-4-mercaptobutylamine as described in Japanese Patent Publication No. 36576/1991, N,N-diethyl-5-mercaptopentylamine, N,N-dimethyl-2,3-dimercaptopropylamine, bis(2-mercaptoethyl)amine, tris(2-mercaptoethyl)amine, N-2-mercaptoethylmorpholine, N,N'-bis(2-mercaptoethyl)-1,4-cyclohexanediamine and N-benzyl-N-methyl-2-mercaptoethylamine as described in Czechoslovakian Patent No. 219,432. As the method where use is made of a strongly acidic ion exchange resin to which a quaternary ammonium salt has been ionically linked, known are those where a strongly acidic ion exchange resin having such an amine ionically linked thereto as N,N,N-trimethyl-2-mercaptoethylammonium, N-(2-hydroxy-3-mercaptopropyl)pyridinium, N-methyl-N-(2-hydroxy-3-mercaptopropyl)morpholium or N-benzyl-N,N-dimethyl-2-mercaptoethylammonium as described in Czechoslovakian Patent No. 184,988. Evaluation as the catalyst with a strongly acidic ion exchange resin of these known mercaptoamines would not be feasible because of the different conditions included in the reactions described in the specifications, although a few bit of information has been given on how the reaction for producing bisphenol A from phenol and acetone depends on the methylene chain length of the alkyl group having a mercapto group and a number of carbon atoms of the alkyl group having no mercapto group. As far as we know, such information can be found only in Japanese Patent Publication No. 36576/1991.

It is described in the Japanese Patent Publication that only two mercaptoalkylamines having a mercaptoalkyl group of a methylene chain of 3 or 4 carbon atoms in the alkyl and an n-propyl group, i.e. N-propyl-3-mercaptopropylamine and N-propyl-4-mercaptobutylamine, have some catalytic activities and catalyst lives for a long period. It is further stated clearly that 3-mercaptopropylamine and 4-mercaptobutylamine, neither of which have a substituent on the nitrogen atom, bring about rapid deactivation in spite of their higher activities at initial stages over the corresponding ones having an n-propyl substituent on the nitrogen atom. In this Japanese Patent Publication, catalytic activities are, however, described only for primary and secondary mercaptoalkylamines, and no description is found for the effect of tertiary amines or quaternary ammonium salts having an increased number of alkyl substituents. Furthermore, it has been found from the evaluation of catalytic capacity of a strongly acidic ion exchange resin to which a variety of well known mercaptoamines have been ionically linked under a constant reaction condition as described later in Comparative Examples that all of these catalysts have problems of low acetone conversion or rapid deactivation of the catalyst.

SUMMARY OF THE INVENTION

The object of the present invention is to provide a strongly acidic ion exchange resin catalyst of a sulfonic acid type which exhibits a high ketone conversion as well as least deactivation and is useful for preparing bisphenols by the economically advantageous condensation reaction of a ketone with a phenol.

We have found that when a variety of mercaptoalkylamines having, on the nitrogen atom, different alkyl groups and different mercaptoalkyl groups in terms of methylene chain lengths in the mercaptoalkyl group was synthesized and ionically bound to a strongly acidic ion exchange resin, which was then evaluated as a catalyst in the reaction for preparing a bisphenol from a phenol and a ketone, high conversion of the ketone and little deactivation of the catalyst were exhibited with mercaptoalkylamines in which both of the hydrogens on the amine nitrogen of the mercaptoalkylamines have a substituent and the mercaptoalkyl group has a methylene chain in the alkyl of a specific length.

Accordingly, the present invention provides a modified ion exchange resin comprising a strongly acidic ion exchange resin of a sulfonic acid type having a specific mercaptoalkylamine ionically bound thereto, which is excellent as a catalyst for preparing a bisphenol by the condensation reaction of a ketone with a phenol. Here, the specific mercaptoalkylamine is the N,N-di-substituted mercaptoalkylamine represented by the formula [0]:

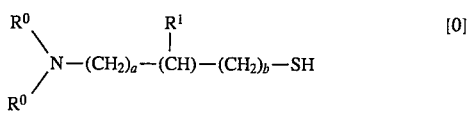

wherein $R^1$ represents a hydrogen atom or an alkyl group having 1–6 carbon atoms, $R^0$s independently represent an alkyl group having 1–10 carbon atoms or the substituents $R^0$ are bonded to each other at their co-terminal to form an alkylene group having 4–5 carbon atoms, a and b independently denote an integer from 0 to 3, and a+b equals to 2 or 3.

As is apparent from the definition of the substituent $R^0$ in the formula [0], these two substituents $R^0$ represent an alkyl group, respectively, or may be bonded to each other at their ω-terminal to form an alkylene group. In the latter case, the alkylene group forms a ring together with the nitrogen atom to which the alkylene group is linked, and the ring is a pyrrolidine ring or a piperidine ring due to the restriction to the carbon atoms in the alkylene group The N,N-di-substituted mercaptoalkylamine of the formula [0] is specifically represented by the following formulae: the N,N-dialkylmercaptoalkylamine represented by the formula:

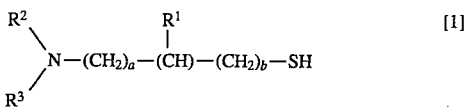

wherein $R^1$ represents a hydrogen atom or an alkyl group having 1–6 carbon atoms, $R^2$ and $R^3$ independently represent an alkyl group having 1–10 carbon atoms, a and b independently denote an integer from 0 to 3, and a+b equals to 2 or 3; and the N-mercaptoalkylpyrrolidine or N-mercaptoalkylpiperidine represented by the formula

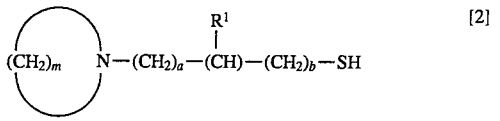

wherein $R^1$ represents a hydrogen atom or an alkyl group having 1–6 carbon atoms, m denotes an integer of 4 or 5, a and b independently denote an integer from 0 to 3, and a+b equals to 2 or 3.

The modified strongly acidic ion exchange resin according to the present invention is distinguished from the conventional known ones in that the mercaptoalkylamine bound thereto is a tertiary amine.

The modified ion exchange resin according to the present invention may be used as a catalyst in the synthesis of a bisphenol by the condensation reaction of a ketone with a phenol with an advantage that it exhibits a high ketone conversion, specifically an acetone conversion, which is sustained for a long period of time.

BRIEF DESCRIPTION OF THE DRAWINGS

FIG. 1 is a graph sowing an acetone conversion vs. reaction time involved obtained in one embodiment of the present invention/Example 21.

PREFERRED EMBODIMENTS OF THE INVENTION

I. Modified ion exchange resins
1. General Description

The modified, viz. mercapto group-containing, ion exchange resin of the present invention is a strongly acidic ion exchange resin of a sulfonic acid type to which a specific mercaptoalkylamine has been ionically bound.

The mercaptoalkylamine is bound to the ion exchange resin generally in a proportion of less than 100 molar % of the sulfonic acid groups and in consideration of the fact that it is to be used as a catalyst for the synthesis of a bisphenol, the proportion may be, for example, 50 molar % or less, particularly 40 molar % or less, as will be described hereinbelow, whereby the modified ion exchange resin may be a mercapto moiety—containing, strongly acidic ion exchange resin.

The mercaptoalkylamine is believed to be ionically bound to the strongly acidic ion exchange resin through the amine nitrogen having a tertiary amine structure which is one of the features of the modified ion exchange resin according to the present invention as described above. One of the three substituents which form the tertiary amine structure of the amine nitrogen atom is a mercaptoalkylamine group. According to the present invention, the mercaptoalkylamine group is also defined specifically as described in detail below.

2. N,N-dialkylmercaptoalkylamine

The N,N-di-substituted mercaptoalkylamines of one family are such that the two substituents on the nitrogen atom other than the mercaptoalkyl group which make the amine nitrogen atom tertiary, viz. $R^0$, are alkyl groups.

The mercaptoalkylamine of this family, the N,N-dialkylmercaptoalkylamine is represented by the formula:

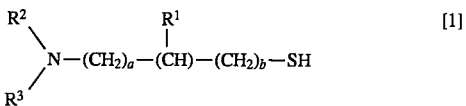

wherein $R^1$ represents a hydrogen atom or an alkyl group having 1–6 carbon atoms, preferably 1–4 carbon atoms, $R^2$ and $R^3$ independently represent an alkyl group having 1–10 carbon atoms, preferably 1–6 carbon atoms, respectively, a and b independently denote an integer from 0 to 3, respectively, and a+b equals to 2 or 3.

Specific example of the N,N-dialkyl-3-mercaptopropylamine wherein a+b=2 include, for example,
N,N-dimethyl-3-mercaptopropylamine,
N,N-diethyl-3-mercaptopropylamine,
N,N-di-n-propyl-3-mercaptopropylamine,
N,N-di-isopropyl-3-mercaptopropylamine,
N,N-di-n-butyl-3-mercaptopropylamine,
N,N-di-n-pentyl-3-mercaptopropylamine,
N,N-di-n-hexyl-3-mercaptopropylamine,
N-methyl-N-ethyl-3-mercaptopropylamine,
N-methyl-N-n-propyl-3-mercaptopropylamine,
N-methyl-N-n-butyl-3-mercaptopropylamine,
N-methyl -N-n-pentyl-3-mercaptopropylamine,
N-methyl-N-n-hexyl-3-mercaptopropylamine,
N-ethyl-N-n-propyl-3-mercaptopropylamine,
N-ethyl-N-n-butyl-3-mercaptopropylamine,
N-ethyl -N-n-pentyl-3-mercaptopropylamine,
N-ethyl-N-n-hexyl-3-mercaptopropylamine,
N-n-propyl-N-n-butyl-3-mercaptopropylamine,
N-n-propyl -N-n-pentyl-3-mercaptopropylamine,
N-n-propyl-N-n-hexyl-3-mercaptopropylamine,
N-n-butyl-N-n-pentyl-3-mercaptopropylamine,
N-n-butyl-N-n-hexyl-3-mercaptopropylamine,
N-n-pentyl-N-n-hexyl-3-mercaptopropylamine,
N,N-dimethyl-1-methyl-3-mercaptopropylamine,
N,N-dimethyl-2-methyl-3-mercaptopropylamine, N,N-dimethyl-3-mercaptobutylamine,
N,N-dimethyl-1-ethyl-3-mercaptopropylamine,
N,N-dimethyl-2-ethyl-3-mercaptopropylamine,
N,N-dimethyl-3-mercaptopentylamine,
N,N-dimethyl-1-propyl-3-mercaptopropylamine,
N,N-dimethyl-2-propyl-3-mercaptopropylamine,
N,N-dimethyl-3-mercaptohexylamine,
N,N-dimethyl-1-butyl-3-mercaptopropylamine,
N,N-dimethyl-2-butyl-3-mercaptopropylamine,
N,N-dimethyl-3-mercaptoheptylamine,
N,N-diethyl-1-methyl-3-mercaptopropylamine,
N,N-diethyl-2-methyl-3-mercaptopropylamine,
N,N-diethyl-3-mercaptobutylamine,
N,N-diethyl-1-ethyl-3-mercaptopropylamine,
N,N-diethyl-2-ethyl-3-mercaptopropylamine,
N,N-diethyl-3-mercaptopentylamine,
N,N-diethyl-1-propyl-3-mercaptopropylamine,
N,N-diethyl-2-propyl-3-mercaptopropylamine,
N,N-diethyl-3-mercaptohexylamine,
N,N-diethyl-1-butyl-3-mercaptopropylamine,
N,N-diethyl-2-butyl-3-mercaptopropylamine,
N,N-diethyl-3-mercaptoheptylamine,
N,N-di-n-propyl-1-methyl-3-mercaptopropylamine,
N,N-di-n-propyl-2-methyl-3-mercaptopropylamine,
N,N-di-n-propyl-3-mercaptobutylamine,
N,N-di-n-propyl-1-ethyl-3-mercaptopropylamine,
N,N-di-n-propyl-2-ethyl-3-mercaptopropylamine,
N,N-di-n-propyl-3-mercaptopentylamine,
N,N-di-n-propyl-1-propyl-3-mercaptopropylamine,
N,N-di-n-propyl-2-propyl-3-mercaptopropylamine,
N,N-di-n-propyl-3-mercaptohexylamine,
N,N-di-n-propyl-1-butyl-3-mercaptopropylamine,
N,N-di-n-propyl-2-butyl-3-mercaptopropylamine,
N,N-di-n-propyl-3-mercaptoheptylamine,
N,N-di-n-butyl-1-methyl-3-mercaptopropylamine,
N,N-di-n-butyl-2-methyl-3-mercaptopropylamine,
N,N-di-n-butyl-3-mercaptobutylamine,
N,N-di-n-butyl-1-ethyl-3-mercaptopropylamine,
N,N-di-n-butyl-2-ethyl-3-mercaptopropylamine,
N,N-di-n-butyl-3-mercaptopentylamine,
N,N-di-n-butyl-1-propyl-3-mercaptopropylamine,
N,N-di-n-butyl-2-propyl-3-mercaptopropylamine,
N,N-di-n-butyl-3-mercaptohexylamine,
N,N-di-n-butyl-1-butyl-3-mercaptopropylamine,
N,N-di-n-butyl-2-butyl-3-mercaptopropylamine and
N,N-di-n-butyl-3-mercaptoheptylamine.

Specific examples of the N,N-dialkyl-4-mercaptobutylamine wherein a+b=3 include, for example,
N,N-dimethyl-4-mercaptobutylamine,
N,N-diethyl-4-mercaptobutylamine,
N,N-di-n-propyl-4-mercaptobutylamine,
N,N-di-isopropyl-4-mercaptobutylamine,
N,N-di-n-butyl-4-mercaptobutylamine,
N,N-di-n-pentyl-4-mercaptobutylamine,
N,N-di-n-hexyl-4-mercaptobutylamine,
N-methyl-N-ethyl-4-mercaptobutylamine,
N-methyl-N-n-propyl-4-mercaptobutylamine,
N-methyl-N-n-butyl-4-mercaptobutylamine,
N-methyl-N-n-pentyl-4-mercaptobutylamine,
N-methyl-N-n-hexyl-4-mercaptobutylamine,
N-ethyl-N-n-propyl-4-mercaptobutylamine,
N-ethyl-N-n-butyl-4-mercaptobutylamine,
N-ethyl-N-n-pentyl-4-mercaptobutylamine,
N-ethyl-N-n-hexyl-4-mercaptobutylamine,
N-n-propyl-N-n-butyl-4-mercaptobutylamine,
N-n-propyl-N-n-pentyl-4-mercaptobutylamine,
N-n-propyl-N-n-hexyl-4-mercaptobutylamine,
N-n-butyl-N-n-pentyl-4-mercaptobutylamine,
N-n-butyl-N-n-hexyl-4-mercaptobutylamine,
N-n-pentyl-N-n-hexyl-4-mercaptobutylamine,
N,N-dimethyl-1-methyl-4-mercaptobutylamine,
N,N-dimethyl-2-methyl-4-mercaptobutylamine,
N,N-dimethyl-3-methyl-4-mercaptobutylamine,
N,N-dimethyl-4-mercaptopentylamine,
N,N-dimethyl-1-ethyl-4-mercaptobutylamine,
N,N-dimethyl-2-ethyl-4-mercaptobutylamine,
N,N-dimethyl-3-ethyl-4-mercaptobutylamine,
N,N-dimethyl-4-mercaptohexylamine,
N,N-dimethyl-1-propyl-4-mercaptobutylamine,
N,N-dimethyl-2-propyl-4-mercaptobutylamine,
N,N-dimethyl-3-propyl-4-mercaptobutylamine,
N,N-dimethyl-4-mercaptoheptylamine,
N,N-dimethyl-1-butyl-4-mercaptobutylamine,
N,N-dimethyl-2-butyl-4-mercaptobutylamine,
N,N-dimethyl-3-butyl-4-mercaptobutylamine,
N,N-dimethyl-4-mercaptobutylamine,
N,N-diethyl-1-methyl-4-mercaptobutylamine,
N,N-diethyl-2-methyl-4-mercaptobutylamine,
N,N-diethyl-3-methyl-4-mercaptobutylamine,
N,N-diethyl-4-mercaptopentylamine,
N,N-diethyl-1-ethyl-4-mercaptobutylamine,
N,N-diethyl-2-ethyl-4-mercaptobutylamine,
N,N-diethyl-3-ethyl-4-mercaptobutylamine,
N,N-diethyl-4-mercaptohexylamine,
N,N-diethyl-1-propyl-4-mercaptobutylamine,
N,N-diethyl-2-propyl-4-mercaptobutylamine,
N,N-diethyl-3-propyl-4-mercaptobutylamine,
N,N-diethyl-4-mercaptoheptylamine,
N,N-diethyl-1-butyl-4-mercaptobutylamine,
N,N-diethyl-2-butyl-4-mercaptobutylamine,
N,N-diethyl-3-butyl-4-mercaptobutylamine,
N,N-diethyl-4-mercaptobutylamine,
N,N-di-n-propyl-1-methyl-4-mercaptobutylamine,
N,N-di-n-propyl-2-methyl-4-mercaptobutylamine,
N,N-di-n-propyl-3-methyl-4-mercaptobutylamine,
N,N-di-n-propyl-4-mercaptopentylamine,
N,N-di-n-propyl-1-ethyl-4-mercaptobutylamine,
N,N-di-n-propyl-2-ethyl-4-mercaptobutylamine,
N,N-di-n-propyl-3-ethyl-4-mercaptobutylamine,
N,N-di-n-propyl-4-mercaptohexylamine,
N,N-di-n-propyl-1-propyl-4-mercaptobutylamine,
N,N-di-n-propyl-2-propyl-4-mercaptobutylamine,
N,N-di-n-propyl-3-propyl-4-mercaptobutylamine,
N,N-di-n-propyl-4-mercaptoheptylamine,
N,N-di-n-propyl-1-butyl-4-mercaptobutylamine,
N,N-di-n-propyl-2-butyl-4-mercaptobutylamine,
N,N-di-n-propyl-3-butyl-4-mercaptobutylamine,
N,N-di-n-propyl-4-mercaptobutylamine,
N,N-di-n-butyl-1-methyl-4-mercaptobutylamine,
N,N-di-n-butyl-2-methyl-4-mercaptobutylamine,
N,N-di-n-butyl-3-methyl-4-mercaptobutylamine,
N,N-di-n-butyl-4-mercaptopentylamine,
N,N-di-n-butyl-1-ethyl-4-mercaptobutylamine,
N,N-di-n-butyl-2-ethyl-4-mercaptobutylamine,
N,N-di-n-butyl-3-ethyl-4-mercaptobutylamine,
N,N-di-n-butyl-4-mercaptohexylamine,
N,N-di-n-butyl-1-propyl-4-mercaptobutylamine,
N,N-di-n-butyl-2-propyl-4-mercaptobutylamine,
N,N-di-n-butyl-3-propyl-4-mercaptobutylamine,
N,N-di-n-butyl-4-mercaptohexylamine,
N,N-di-n-butyl-1-butyl-4-mercaptobutylamine,
N,N-di-n-butyl-2-butyl-4-mercaptobutylamine,
N,N-di-n-butyl-3-butyl-4-mercaptobutylamine, and
N,N-di-n-butyl-4-mercaptobutylamine.

3. N-mercaptoalkylpyrrolidine and N-mercaptoalkylpiperidine

The mercaptoalkylamines according to the present invention of another family is such that the two substituents $R^0$ are bonded to each other at their ω-terminal to form, together with the nitrogen atom, a heterocyclic ring, i.e. a pyrrolidine ring or a piperidine ring.

Accordingly, the N-mercaptoalkylpyrrolidine and the N-mercaptoalkylpiperidine of this family are represented by the formula:

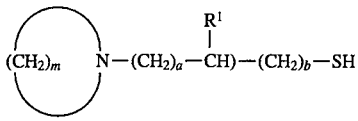 [2]

wherein $R^1$ represents a hydrogen atom or an alkyl group having 1–6 carbon atoms, preferably 1–4 carbon atoms, m denotes an integer of 4 or 5, a and b independently represent an integer from 0 to 3, respectively, and a+b equals to 2 or 3.

Specific examples of the N-mercaptoalkylpyrrolidine wherein m=4 includes, for example,
N-3-mercaptopropylpyrrolidine,
N-(1-methyl-3-mercaptopropyl)-pyrrolidine,
N-(2-methyl-3-mercaptopropyl)pyrrolidine,
N-3-mercaptobutyl-pyrrolidine,
N-(1-ethyl-3-mercaptopropyl)pyrrolidine,
N-(2-ethyl-3-mercaptopropyl)pyrrolidine,
N-3-mercaptopentylpyrrolidine,
N-(1-propyl-3-mercaptopropyl)pyrrolidine,
N-(2-propyl-3-mercaptopropyl)pyrrolidine,
N-3-mercaptohexylpyrrolidine,
N-(1-butyl-3-mercaptopropyl)-pyrrolidine,
N-(2-butyl-3-mercaptopropyl)pyrrolidine,
N-3-mercaptoheptylpyrrolidine,
N-(4-mercaptobutyl)pyrrolidine,
N-(1-methyl-4-mercaptobutyl)pyrrolidine,
N-(2-methyl-4-mercaptobutyl)pyrrolidine,
N-(3-methyl-4-mercaptobutyl)pyrrolidine,
N-(4-mercaptopentyl)-pyrrolidine,
N-(1-ethyl-4-mercaptobutyl)pyrrolidine,
N-(2-ethyl-4-mercaptobutyl)pyrrolidine,
N-(3-ethyl-4-mercaptobutyl)pyrrolidine,
N-(4-mercaptohexyl)pyrrolidine,
N-(1-propyl-4-mercaptobutyl)pyrrolidine,
N-(2-propyl-4-mercaptobutyl)pyrrolidine,
N-(3-propyl-4-mercaptobutyl)pyrrolidine,
N-(4-mercaptoheptyl)pyrrolidine,
N-(1-butyl-4-mercaptobutyl)pyrrolidine,
N-(2-butyl-4-mercaptobutyl)pyrrolidine,
N-(3-butyl-4-mercapto-butyl)pyrrolidine and
N-(4-mercaptooctyl)pyrrolidine.

Specific examples of the N-mercaptoalkylpiperidine wherein m=5 includes, for example,
N-3-mercaptopropylpiperidine,
N-(1-methyl-3-mercaptopropyl)piperidine,
N-(2-methyl-3-mercaptopropyl)piperidine,
N-3-mercaptobutylpiperidine,
N-(1-ethyl-3-mercaptopropyl)piperidine,
N-(2-ethyl-3-mercaptopropyl)piperidine,
N-3-mercaptopentyl-piperidine,
N-(1-propyl-3-mercaptopropyl)piperidine,
N-(2-propyl-3-mercaptopropyl)piperidine,
N-3-mercaptohexylpiperidine,
N-(1-butyl-3-mercaptopropyl)-piperidine,
N-(2-butyl-3-mercaptopropyl)piperidine,
N-3-mercaptoheptylpiperidine,
N-(4-mercaptobutyl)piperidine,
N-(1-methyl-4-mercaptobutyl)piperidine,
N-(2-methyl-4-mercaptobutyl)piperidine,
N-(3-methyl-4-mercaptobutyl)piperidine,
N-(4-mercaptopentyl)-piperidine,
N-(1-ethyl-4-mercaptobutyl)piperidine,
N-(2-ethyl-4-mercaptobutyl)piperidine,
N-(3-ethyl-4-mercaptobutyl)piperidine,
N-(4-mercaptohexyl)piperidine,
N-(1-propyl-4-mercaptobutyl)piperidine,
N-(2-propyl-4-mercaptobutyl)piperidine,
N-(3-propyl-4-mercaptobutyl)piperidine,
N-(4-mercaptoheptyl)piperidine,
N-(1-butyl-4-mercaptobutyl)piperidine,
N-(2-butyl-4-mercaptobutyl)piperidine,
N-(3-butyl-4-mercaptobutyl)piperidine and
N-(4-mercaptooctyl)piperidine.

4. Synthesis of the mercaptoalkylamine

The mercaptoalkylamines used in the ion exchange resin according to the present invention may be prepared in a variety of ways and can be the ones prepared by any methods. As an illustrative therefor, the mercaptoalkylamine can be prepared by reacting the corresponding chloroalkylamine hydrochloride with sodium thiosulfate to form a Bunte salt, which is acid-decomposed to give a disulfide product of the N,N-dialkylmercaptoalkylamine, which is further subjected to reduction. The N-mercaptoalkylpyrrolidines and N-mercaptoalkylpiperidines can also be prepared in the same manner. Other methods may be mentioned such that a thioacetate ester derived from a chloroalkylamine and potassium thioacetate is hydrolyzed or that an isothiuronium salt derived from a chloroalkylamine and thiourea is decomposed under alkaline conditions.

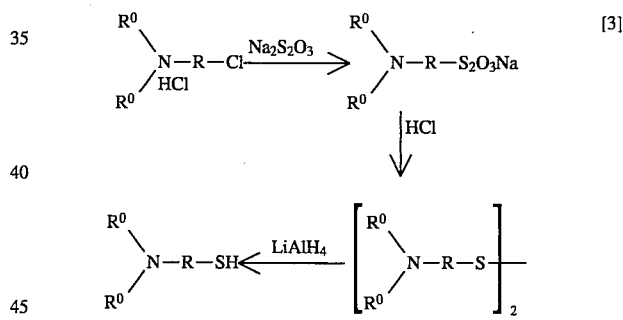 [3]

4. A strongly acidic ion exchange resin of a sulfonic acid type

The ion exchange resin to which a mercaptoalkylamine is to be ionically bound is a strongly acidic ion exchange resin having a sulfonic acid group as a ion exchange group.

Such strongly acidic ion exchange resin is well known in the art, and there are various types of resin including matrixes supporting the sulfonic acid group thereon, either of which can be used in the present invention.

Among these ion exchange resins, the most typical one which is preferably used is a strongly acidic ion exchange resin comprising a sulfonated product of a styrene-divinyl benzene copolymer. The copolymer has a divinyl benzene unit in a proportion of 1–40%, preferably 1–20%, particularly 1–10%. The ion exchange resin preferably has an exchange capacity of 0.5–4.0 meq/ml in the hydrous state and 2.0–7.0 meq/g in the dry state. The ion exchange resin preferably has a particle size distribution in which 95% or more of the resin having 100–3,000 μm is included. Strongly acidic ion exchange resins are classified into three types, namely gel, porous and high porous types on the basis of their physical properties. Any type of these resins can be used but the gel and porous types are preferred in the present invention. Specifically, typical resins include, for example, Amberlyst 15, 31 and 32 (trade names, manufactured by Rohm & Haas), Dowex 50w and 88 (trade names, manufactured by Dow Chemical), and Diaion SK1B, SK102, SK104, PK208 and PK212 (trade names, manufactured by Mitsubishi Chemical). These ion exchange resins are used in an acid form. The sulfonate form such as sodium salt is generally treated with an acid such as hydrochloric acid to convert the salt substantially into the acid, that is 90% or more of its total exchange capacity is converted into an acid form for use. These ion exchange resins are commercially available generally in a hydrous state, which can be directly used for the ionical binding of the aforementioned mercaptoalkylamine without special treatment such as dehydration or the like.

5. Preparation of modified ion exchange resin

The ionic adduct of the mercaptoalkylamine with the strongly acidic ion exchange resin of a sulfonic acid type can be prepared by any method which assures the formation of the ionic binding of the tertiary amine nitrogen in the mercaptoalkylamine to the sulfonic acid groups.

The amine reactant and the sulfonic acid reactant may be directly reacted with each other, or either or both of these reactants are converted into their functional derivatives before the reaction, and the reaction product may, upon necessity, be treated so that the product will recover from the functional derivative.

Accordingly, the strongly acidic ion exchange resin having the mercaptoalkylamine ionically bound can thus be prepared by a method which comprises dissolving a mercaptoalkylamine in an aqueous solution of an acid having a pKa larger than that of sulfonic acid such as acetic acid, trifluoroacetic acid or monochloroacetic acid through formation of a salt of the amine with the acid to form an aqueous solution of the salt, adding the solution to an aqueous dispersion of a strongly acidic ion exchange resin, and agitating the dispersion for an appropriate period, e.g. 0.1–10 hours.

Alternatively, it is possible to form the ionic binding desired by the method which comprises dissolving the mercaptoalkylamine in a solvent for the amine such as an alcohol, a ketone or an ether, adding the amine solution to a dispersion of a strongly acidic ion exchange resin dispersed in the same solvent, and agitating the mixture for an appropriate period, e.g. 0.1–10 hours. The preferred solvent includes methanol, ethanol, isopropanol, acetone, 1,4-dioxane and tetrahydrofuran. These solvents may or may not contain water, for example in an amount of 0–60% by weight.

Another alternative for ionically binding the amine to the ion exchange resin is carry out the binding on the precursor of the amine.

More particularly, as described hereinabove, one of the methods for preparing the mercaptoalkylamine is a process which comprises preparing a disulfide derivative as a precursor to the mercaptoalkylamine and subjecting the precursor to hydrogenolysis. It is then possible to incorporate, into the process, a step for forming the ionic binding with the strongly acidic ion exchange resin, in such a way that the mercaptoalkylamine in the form of a disulfide as a precursor thereof is dissolved in an organic solvent such as an alcohol, a keton or an ether, adding the solution to a dispersion of the strongly acidic ion exchange resin in the same solvent, agitating the mixture for 0.1–2 hours to form an ion exchange resin to which the disulfide is ionically bound, and reducing the disulfide with a reducing agent such as triphenylphosphine or the like thereby to form the strongly acidic ion exchange resin having the mercaptoalkylamine ionically bound. The preferred solvent for the contact of the disulfide precursor with the ion exchange resin includes methanol, ethanol, isopropanol, acetone, 1,4-dioxane and tetrahydrofuran. These solvents may contain water, for example in an amount of 0–60% by weight.

The amount of the N,N-dialkylmercaptoalkylamine, N-mercaptoalkylpyrrolidine and N-mercaptoalkylpiperidine used for the formation of the ionic binding to the strongly acidic ion exchange resin is generally in a proportion of 3–40 molar %, preferably 5–30 molar % to the total amount of the sulfonic acid groups in the strongly acidic ion exchange resin. If the amount of the ionic binding is less than 3 molar %, the catalytic effect by the mercaptoalkylamine bound to the ion exchange resin may not be sufficiently exhibited on the condensation reaction of a phenol with a ketone; if the amount is more than 40 molar %, the catalytic effect is undesirably lowered by the decrease of the amount of sulfonic acid.

II. Use of the modified ion exchange resin/preparation of bisphenols

1. General description

As described above, the preparation of a bisphenol by the condensation reaction of a phenol with a ketone is known in the art, and it is also known in the art to conduct the condensation reaction in the presence of a catalyst.

An illustrative example of the use of the modified ion exchange resin, namely the ionic adduct of the mercaptoalkylamine-strongly acidic ion exchange resin of a sulfonic acid type, is its use as a catalyst of the aforementioned condensation reaction. Accordingly, the present invention features a process for preparing a bisphenol catalyzed by the ionic adduct.

The process for preparing the bisphenol according to the present invention is essentially the same as the conventionally well known process described above except that the catalyst used is a special ionic adduct.

2. Phenols

Condensation of a ketone with a phenol is assumed to utilize the strong ortho or para orientation, particularly the para orientation, of a phenolic hydroxyl group, so that the phenol used which can have a substituent on it should be the one which has no substituent at the ortho or para position. Since 4,4'-bisphenols are generally preferred in view of the uses of a bisphenol, a phenol having no substituent at the para position thereby forming a 4,4'-bisphenol is preferred. The substituent that a phenol can carry may be anyone provided that it does not inhibit the ortho and para orientations of the phenolic hydroxyl group and it does not place steric hindrance to the condensation position of the ketone. Typical substituent includes a lower hydrocarbyl group, for example a $C_1$–$C_4$ alkyl group, particularly a methyl group, and a halogen atom, for example, a fluorine atom and a chlorine atom, particularly a chlorine atom.

Specific examples of the phenols for the present invention include, for example, a non-substituted phenol, o- and m-cresols, 2,5- and 2,6-xylenols, 2,3,6-trimethylphenol, 2,6-di-tert-butylphenol, o- and m-chlorophenols, 2,5- and 2,6-dichlorophenols. Among these phenols, the non-substituted phenol is particularly preferred.

3. Ketone

The ketone which can be used in the method where use is made of the modified ion exchange resin in accordance with the present invention includes, for example, acetone, methyl ethyl ketone, diethyl ketone, methyl isobutyl ketone, cyclohexanone and acetophenone. Among these ketones, acetone is particularly preferred.

4. Condensation

When the strongly acidic ion exchange resin having the mercaptoalkylamine ionically bound thus prepared (referred to hereinafter as catalyst resin) is used for the condensation reaction of a ketone with a phenol, it may be preferable to pass the phenol through the reaction system as a preliminary procedure at a volume of 5–200 times of the catalyst resin at a liquid hourly space velocity (LHSV) of 0.5–50 hr$^{-1}$ at a temperature of 40°–110° C. The solvent is successfully exchanged from water to the phenol by the procedure and thus can be used in the reaction without an induction period.

The mode of the reaction is not specifically limited and the reaction may be generally carried out by any methods such as continuous methods where the catalyst is in a fixed bed, in a fluidized bed or in a bed agitated by a stirrer or batch methods. When the reaction is conducted in the continuous way on the fixed bed, the fluidized bed or the bed agitated, the mixture of starting materials is generally supplied at an LHSV of 0.05–20 hr$^{-1}$, preferably 0.2–10 hr$^{-1}$ on the basis of the catalyst resin which has been wetted with a phenol used. The reaction is generally conducted at a temperature of 40°–120° C., preferably 60°–100° C. If the reaction is carried out at a temperature of 40° C. or lower, the reaction proceeds only slowly; at a temperature of 120° C. or higher, the modified resin is significantly deteriorated and by-products or colored products may undesirably be increased.

The molar ratio of the phenol to the ketone is generally in a proportion of 2–40 moles, preferably 4–30 moles, of the phenol to 1 mole of the ketone. If the phenol is used in an amount smaller than that described above, by-products may unpreferably be increased; even if the phenol is used in an amount of more than 40 moles, the effect is not improved but the reaction is not economical because of the increased amount of the phenol to be recovered for recycling. The bisphenol as the product desired, for example bisphenol A, can be isolated and purified by the well known method such that the unreacted phenol is recovered, the bisphenol A/phenol adduct is isolated and then the phenol is recovered from the adduct by the procedure such as distillation or the like.

EXAMPLES

The present invention is now described in more detail with reference to Examples and Comparative Examples, where the acetone conversion, the selectivity of 4,4'-bisphenol A (referred to hereinafter as 4,4'-BPA), the % modification and the % residual sulfonic acid are calculated on the following equations and expressed by percentage.

Acetone conversion =

$$\frac{\text{(Amount of acetone supplied} - \text{Amount of unreacted acetone)}}{\text{Amount of acetone supplied}} \times 100$$

4,4'-BPA selectivity =

$$\frac{\text{Molar amount of produced 4,4'-BPA}}{\text{Molar amount of acetone consumed in reaction}} \times 100$$

% Modification =

$$\frac{\text{Molar amount of ionically bound mercaptoalkylamine}}{\text{Molar amount of total SO}_3\text{H group before reaciton}} \times 100$$

% Residual sulfonic acid group =

$$\frac{\text{Molar amount of total SO}_3\text{H group after modification}}{\text{Molar amount of total SO}_3\text{H group before modification}} \times 100$$

Example 1

In a 300 ml round-bottom flask were charged 31.6 g of N,N-dimethyl-3-chloropropylamine hydrochloride, 34.8 g of sodium thiosulfate and 100 ml of distilled water. The mixture was heated under reflux and stirred for 2 hours and then continuously heated under reflux for further 1 hour after the addition of 22.3 g of 36% hydrochloric acid. Under cooling in an ice bath, 25.3 g of 95% sodium hydroxide was slowly added to adjust pH to the alkaline range, and the mixture was subjected to extraction three times with 30 ml of tetrahydrofuran. Most of the water was removed with potassium hydroxide pellets. The extract was further dehydrated with anhydrous potassium carbonate, and the solvent was removed by distillation and distilled under reduced pressure to give a transparent colorless bis(N,N-dimethyl-3-aminopropyl)disulfide as the precursor of the mercaptoalkylamine desired in an amount of 22.5 g.

In a 200 ml round-bottom flask were charged 0.44 g of lithium aluminum hydride and 50 ml of anhydrous ethyl ether, and a 2.75 g portion of bis(N,N-dimethyl-3-aminopropyl)disulfide dissolved in 20 ml of anhydrous ethyl ether was added dropwise over a period of 30 minutes. After the reaction mixture was further heated under reflux for 1 hour and ice-cooled, 0.63 g of ion exchanged water was slowly added, and 1.4 g of acetic acid was added. 2.0 g of anhydrous magnesium sulfate was added and the mixture was stirred for 10 minutes, followed by removal of the solid matter. To the solution in ethyl ether obtained was added 150 g of ion exchanged water and 1.4 g of acetic acid, and the ethyl ether was removed by distillation under reduced pressure to give 156.2 g of an aqueous solution of N,N-dimethyl-3-mercaptopropylamine acetate. Titration with potassium iodate proved that the solution contained 21.0 mmole of N,N-dimethyl-3-mercaptopropylamine acetate.

A 87 g portion of the aqueous solution was added dropwise to a slurry containing 40 g of Amberlyst 31 (strongly acidic sulfonic acid ion exchange resin in a gel form having exchange capacity of 1.80 meq/wet-g, manufactured by Rohm & Haas) dispersed in 80 ml of ion exchanged water, and the mixture was further stirred at room temperature for 1 hour. The ion exchange resin was charged in a glass column, and ion exchanged water was passed through the column at an LHSV of 2 hr$^{-1}$ until the effluent had a pH of 7. Filtration gave 40.5 g of the modified Amberlyst 31. The modified resin was titrated for the determination of the contents of the mercapto group and sulfonic acid group to give a % modification of 12.8% and a % residual sulfonic acid of 87.0%.

A 14 ml portion of the modified Amberlyst 31 was charged in a stainless column having an internal diameter of 7.6 mm and a length of 320 mm, and phenol was passed through the column at a temperature of 70° C. at an LHSV of 2 hr$^{-1}$ for 24 hours. The modified resin at this point had a volume of about 10.5 ml. The mixture of phenol/acetone= $^{10}/_1$ (molar ratio) was passed through the column at 70° C. and 1.0 hr$^{-1}$ of LHSV on the basis of the modified resin wetted with phenol for continuous reaction for 300 hours. The acetone conversion was 92.7% and the 4,4'-BPA selectivity was 92.9% at 40 hours after the reaction was started, and the acetone conversion was 92.2% and the 4,4'-BPA selectivity was 93.4% after 300 hours.

Example 2

To a suspension of 25 g of Amberlyst 31 in a mixed solvent of 50 ml of 1,4-dioxane and 25 ml of ion exchanged water was added a solution of 0.79 g of the precursor prepared in Example 1, that is bis(N,N-dimethyl-3-aminopropyl)disulfide in 10 ml of 1,4-dioxane to ionically bind the disulfide to the ion exchange resin. Triphenylphosphine (1.76 g) was added, and the resulting mixture was stirred under heating at 70° C. under a nitrogen atmosphere for 3 hours to reduce the disulfide on the ion exchange resin. After the mixture was cooled to room temperature and charged in a glass column, the mixtures of 100 ml of 1,4-dioxane and 50 ml of ion exchanged water and of 50 ml of 1,4-dioxane and 100 ml of ion exchanged water, and 200 ml of ion exchanged water were passed through the column in this sequence at a LHSV of 2 $hr^{-1}$. Filtration of the column content gave the modified Amberlyst 31 in a yield of 25.6 g. The modified resin was titrated for the determination of the contents of the mercapto group and sulfonic acid group to give a % modification of 12.6% and a % residual sulfonic acid of 87.3%. The modified resin was used for the evaluation of the bisphenol synthesis reaction under the same conditions as in Example 1. The results are shown in Table 1.

Example 3

To a solution of 2.36 g of the bis-precursor prepared in Example 1, that is (N,N-dimethyl-3-aminopropyl)disulfide, in a mixed solvent of 50 ml of 1,4-dioxane and 25 ml of ion exchanged water, 2.6 g of triphenylphosphine was added, and the mixture was heated and stirred at 60° C. under a nitrogen atmosphere to reduce the disulfide into N,N-dimethyl-3-mercaptopropylamine.

The solution was added to a slurry containing 55.5 g of Amberlyst 31 which had previously suspended in a mixed solvent of 50 ml of 1,4-dioxane and 25 ml of ion exchanged water, and the mixture was stirred at room temperature for 30 minutes. Ion exchange resin was collected by filtration and charged in a glass column, and 200 ml of a mixed solvent of 1,4-dioxane/ion exchanged water=½ was passed through the column to wash completely the triphenylphosphine and its oxide derivative. Furthermore, 500 ml of ion exchanged water was passed at an LHSV of 1 $hr^{-1}$ for replacing the solvent. Filtration of the content in the column gave 55.2 g of the modified Amberlyst 31, which was found upon titration to have a % modification of 19.6% and a % residual sulfonic acid of 80.0%.

The modified Amberlite 31 in an amount of 30 ml was charged in a stainless column having an internal diameter of 10.7 mm and a length of 600 mm, and phenol was passed at an LHSV of 5 $hr^{-1}$ for 24 hours. The modified resin at this point had a volume of about 22.5 ml. A mixture of phenol/acetone=10/1 (molar ratio) was passed at 70° C. and an LHSV of 1.0 $hr^{-1}$ on the basis of the modified resin wetted with phenol for 300 hour continuous reaction. The results are shown in Table 1.

Examples 4–10

In the same manner as in Example 1, the modified products of Amberlyst 31 were prepared wherein N,N-dialkyl-3-mercaptopropylamines and N,N-dialkyl-4-mercaptobutylamines were synthesized from a variety of N,N-dialkylchloroalkylamine hydrochlorides. The bisphenol synthesis reactions were evaluated with these modified resins under the same conditions as in Example 1. The results are shown in Table 1. The symbols, a, b, $R^1$, $R^2$ and $R^3$ in Table 1 correspond to those in Formula [1], respectively.

Comparative Example 1

A solution of 0.85 g of a commercially available 2-aminoethanethiol in 20 ml of ion exchanged water containing 0.65 g of acetic acid was added dropwise over a period of 30 minutes to a slurry containing 30 g of Amberlyst 31 suspended in 60 ml of ion exchanged water, and the mixture was further stirred for 1 hour at room temperature. After the ion exchange resin was charged in a glass column and ion exchanged water was passed through the column at an LHSV of 2 $hr^{-1}$ until the effluent had a pH of 7, the content in the column was collected by filtration to give 30.4 g of the modified Amberlyst 31. The modified resin was titrated for the determination of the contents of the mercapto group and sulfonic acid group to give a % modification of 20.0% and a % residual sulfonic acid of 79.7%.

The bisphenol synthesis reactions were evaluated with these modified resin under the same conditions as in Example 1. The results at 40 hours and 300 hours after the reaction was started are shown in Table 2.

Comparative Example 2

In a 100 ml round-bottom flask, 8.5 g of N,N-dimethyl-2-chloroethylamine hydrochloride, 8.7 g of sodium thiosulfate and 50 ml of distilled water were charged and heated under reflux for 2 hours. 36% hydrochloric acid (5.1 g) was added, and the mixture was further heated under reflux for 1 hour. With cooling the mixture on an ice bath, 5.5 g of sodium hydroxide was slowly added to make the mixture alkaline, which was then subjected to extraction twice with 50 ml of ethyl acetate. After desiccating with anhydrous potassium carbonate, the solvent was removed by distillation and distilled under reduced pressure to give 7.0 g of bis(N,N-dimethyl-2-aminoethyl)disulfide, the precursor.

To the solution of 1.2 g of the disulfide precursor in 30 ml of isopropanol was added 1.6 g of dimethyl sulfate, and the mixture was stirred at 60° C. for 2 hours. The solvent was then removed by distillation to give 2.6 g of bis(N,N,N-trimethyl-2-ethylammonium)disulfide bismethylsulfate as a white crystal. The crystal was dissolved in 50 ml of ion exchanged water and passed through a column having charged therein 100 ml of a strongly basic ion exchange resin Diaion PA 306 (trade name, manufactured by Mitsubishi Chemical), which had preliminarily changed into the acetate type, at an LHSV of about 0.5 $hr^{-1}$, and 150 ml of ion exchanged water was further passed through the column to exchange the counter anion of the disulfide from methylsulfate into acetate. To the aqueous solution of the disulfide thus recovered were added 100 ml of 1,4-dioxane and 6.3 g of triphenylphosphine, and the mixture was stirred and heated at 60° C. under a nitrogen atmosphere for 3 hours.

The solution was added to a slurry containing 30 g of Amberlyst 31 which had preliminarily suspended in a mixed solvent of 100 ml of 1,4-dioxane and 50 ml of ion exchanged water, and the mixture was stirred at 60° C. for 2 hours. After cooling to room temperature, the ion exchange resin was collected by filtration and charged in a glass column, and 100 ml of a mixture of 1,4-dioxane/ion exchanged water=½ was passed through the column, followed by 200 ml of ion exchanged water at an LHSV of 1 $hr^{-1}$. Filtration of the content in the column gave 29.8 g of the modified Amberlyst 31. The modified resin was titrated for the determination of the contents of the mercapto group and sulfonic acid group to give a % midification of 20.0% and a % residual sulfonic acid of 79.9%.

The bisphenol synthesis reactions were conducted with the modified resin under the same conditions as in Example 1. The results at 40 hours and 300 hours after the reaction was started are shown in Table 2.

Comparative Examples 3–4

Either one of the disulfides synthesized from N-methyl-3-chloropropylamine hydrochloride and N-n-propyl-3-chloropropylamine hydrochloride was subjected to reaction in the same manner as in Example 2 to give the modified products of Amberlyst 31 having the corresponding mercaptoalkylamine ionically bound. The bisphenol synthesis reactions were evaluated with these modified resins under the same conditions as in Example 1. The results at 40 hours and 300 hours after the reaction was started are shown in Table 2.

Comparative Examples 5–7

In the same manner as in Example 1, a variety of N,N-dialkylchloroalkylamine hydrochlorides were subjected to reaction to give the modified products of Amberlyst 31 having the corresponding mercaptoalkylamine ionically bound. The bisphenol synthesis reactions were evaluated with these modified resins under the same conditions as in Example 1. The results at 40 hours and 300 hours after the reaction was started are shown in Table 2. The symbols, a, b, $R^1$, $R^2$ and $R^3$ in Table 2 correspond to those in formula 1, except that the quaternary mercaptoalkylammonium salt in Comparative Example 2 is represented by the formula:

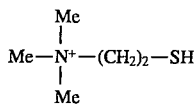

[4]

Examples 11–13

In the same manner as in Example 1, N-3-chloropropylpyrrolidine hydrochloride, N-3-chloropropylpiperidine hydrochloride and N-4-chlorobutylpyrrolidine hydrochloride, respectively, were subjected to reaction to give the corresponding N-3-mercaptopropylpyrrolidine, N-3-mercaptopropylpiperidine and N-4-mercaptobutylpyrrolidine for preparing the modified products of Amberlyst 31. The bisphenol synthesis reactions were evaluated with these modified resins under the same conditions as in Example 1. The results are shown in Table 3. The symbols, a, b and m in Table 1 correspond to those in formula [2].

Comparative Examples 8–9

In the same manner as in Example 1, N-3-chloropropylmorpholine hydrochloride and N-3-chloropropylhexamethyleneimine hydrochloride, respectively, were subjected to reaction to give the corresponding N-3-mercaptopropylmorpholine and N-3-mercaptopropylhexamethyleneimine, and the modified products of Amberlyst 31. The bisphenol synthesis reactions were evaluated with these modified resins under the same conditions as in Example 1. The results are shown in Table 3. The symbols, a, b and m in Table 3 correspond to those in formula [2], except that N-3-mercaptopropylmorpholine is represented by the formula:

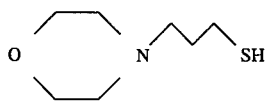

[5]

Examples 14–20

Each of a variety of N,N-dialkylchloroalkylamine hydrochlorides was subjected to reaction in the same manner as in Example 1 except that Diaion SK-104H (manufactured by Mitsubishi Chemical; strongly acidic ion exchange resin of a sulfonic acid type, in a gel form having exchange capacity: 1.55 meq/wet-g, Examples 14–19) and Diaion PK-208H (manufactured by Mitsubishi Chemical; strongly acidic ion exchange resin of a sulfonic acid type, in a porous form having exchange capacity: 1.65 meq/wet-g, Example 20) to give the corresponding N,N-dialkyl-3-mercaptopropylamine and N,N-dialkyl-4-mercaptobutylamine for preparing the modified ion-exchanged resins. The hisphenol synthesis reactions were evaluated with these modified resins under the same conditions as in Example 1 except the LHSV. The results are shown in Table 4. The symbols, a, b, $R^1$, $R^2$ and $R^3$ in Table 4 correspond to those in formula 1.

As is apparent from Examples and Comparative Examples, when that the mercaptoalkyl group has a methylene chain of 2 or 6 carbon atoms between the nitrogen atom and the mercapto group or when a hydrogen atom is present on the nitrogen atom (Comparative Examples 1–5 and 7), the acetone conversions remain low, for example in the range of 66–86%, and when that the mercaptoalkyl group has a methylene chain of 5 carbon atoms between the nitrogen atom and the mercapto group (Comparative Example 6), while the acetone conversion was initially maintained at a high level, it is decreased by about 6% from 40 hours to 300 hours and thus the catalyst activity was greatly decreased. When the N,N-dialkylmercaptoalkylamine has no hydrogen on the nitrogen atom and the mercaptoalkyl group has a methylene chain of 3 or 4 carbon atoms between the nitrogen atom and the mercapto group, the acetone conversion is maintained at a high level of 90% or more and the catalyst activity is decreased little even after 300 hours. Also, in the case of a mercaptoalkylamine having a cyclic amine structure, the acetone conversion is maintained at a high level only when the cyclic amine is pyrrolidine or piperidine.

Example 21

A 80 ml of volume of Amberlyst 31 having N,N-dimethyl-3-mercaptopropylamine (a=2, b=0, $R^2$=H, $R^2$=$R^3$=Me in formula [1]) ionically bound (a % modification: 12.9%; a % residual sulfonic acid: 87.0%) was charged in a stainless column having an internal diameter of 22 mm and a length of 400 mm, and phenol was passed at 70° C. and an LHSV of 1 hr$^{-1}$ for 48 hours. At this point, the modified resin had a volume of about 60 ml. Then, the mixture of phenol/acetone=$^{10}$/$_1$ (molar ratio) was passed through the column at 70° C. and an LHSV of 1.0 hr$^{-1}$ on the basis of the phenol-wetted modified resin for 2,000 hour continuous reaction. The relationship between the reaction period and the acetone conversion is illustrated in FIG. 1. The acetone conversion was not decreased and the catalyst activity was also maintained at a high level even after 2,000 hour reaction.

It may be assumed that the condensation reaction of phenol with acetone may be inhibited by the water formed upon the condensation reaction. In order to confirm this, several strongly acidic ion exchange resin of a sulfonic acid type having an ionically bound mercaptoalkylamine of various methylene length between the nitrogen atom and the mercapto group were used in the condensation reaction thereby to determine how the inhibition may depend on the methylene length in view of the acetone conversion.

Reference Examples 1–3

In a 50 ml flask were added 4 g of hydrated Diaion SK-104H having an ionically bound mercaptoalkylamine selected from those set forth in Table 5 and 30 g of phenol, followed by agitation at 70° C. for 1 hour and then by decantation to discard the phenol. This procedure was repeated 4 times to reduce the content of water to no higher than 0.1% by weight.

To the ion exchange resin thus rinsed was added 10.8 g of a fresh batch of phenol, followed by agitation at 70° C., then by addition of 0.67 g of acetone. The mixture was agitated for 30 minutes, and the acetone conversion was then determined by gas chromatography.

In order to make it clearer how the condensation reaction may be inhibited by the water formed upon the condensation reaction, the similar run was carried out except for the use of 0.2 g of ion-exchanged water in addition to 0.67 g of acetone, and the acetone conversion after 30 minutes agitation was determined.

The results obtained are set forth in Table 5.

TABLE 1

| | Example | | | | | | | | | |
|---|---|---|---|---|---|---|---|---|---|---|
| | 1 | 2 | 3 | 4 | 5 | 6 | 7 | 8 | 9 | 10 |
| a (Formula 1) | 2 | 2 | 2 | 2 | 3 | 3 | 3 | 3 | 2 | 1 |
| b (Formula 1) | 0 | 0 | 0 | 0 | 0 | 0 | 0 | 0 | 1 | 2 |
| $R^1$ (Formula 1) | H | H | H | H | H | H | H | H | Me | n-Bu |
| $R^2$ (Formula 1) | Me | Me | Me | Et | Me | Et | n-Bu | n-Hex | n-Bu | n-Bu |
| $R^3$ (Formula 1) | Me | Me | Me | Et | Me | Et | n-Bu | n-Hex | n-Bu | n-Bu |
| % Modification (%) | 12.8 | 12.6 | 19.6 | 15.0 | 15.0 | 13.7 | 14.0 | 15.1 | 16.2 | 15.7 |
| % Residual sulfonic acid (%) After 40 hours | 87.0 | 87.3 | 80.0 | 82.0 | 85.0 | 85.7 | 82.0 | 82.8 | 83.5 | 84.3 |
| Acetone conversion (%) | 92.7 | 91.1 | 96.8 | 90.7 | 95.7 | 93.3 | 93.1 | 93.6 | 92.6 | 92.1 |
| 4,4'-BPA Selectivity (%) | 92.9 | 93.7 | 93.9 | 93.3 | 93.5 | 94.8 | 93.4 | 95.3 | 93.2 | 93.5 |
| After 300 hours | | | | | | | | | | |
| Acetone conversion (%) | 92.2 | 91.1 | 96.0 | 90.4 | 95.2 | 93.7 | 93.8 | 92.9 | 92.2 | 91.5 |
| 4,4'-BPA Selectivity (%) | 93.4 | 93.5 | 93.8 | 93.2 | 94.0 | 94.9 | 93.3 | 94.2 | 93.5 | 93.7 |

TABLE 2

| | Comparative Example | | | | | | |
|---|---|---|---|---|---|---|---|
| | 1 | 2 | 3 | 4 | 5 | 6 | 7 |
| a (Formula 1) | 1 | (Formula 4) | 2 | 2 | 1 | 4 | 5 |
| b (Formula 1) | 0 | (Formula 4) | 0 | 0 | 0 | 0 | 0 |
| $R^1$ (Formula 1) | H | (Formula 4) | H | H | H | H | H |
| $R^2$ (Formula 1) | H | (Formula 4) | Me | n-Pr | Me | n-Bu | Me |
| $R^3$ (Formula 1) | H | (Formula 4) | H | H | Me | n-Bu | Me |
| % Modification (%) | 20.0 | 20.0 | 19.0 | 19.5 | 20.3 | 18.7 | 14.9 |
| % Residual sulfonic acid (%) After 40 hours | 79.7 | 79.9 | 80.5 | 80.0 | 79.3 | 81.5 | 84.8 |
| Acetone conversion (%) | 80.5 | 67.3 | 86.0 | 80.3 | 81.4 | 94.5 | 78.2 |
| 4,4'-BPA Selectivity (%) | 92.6 | 92.0 | 94.1 | 94.5 | 93.0 | 94.8 | 94.3 |
| After 300 hours | | | | | | | |
| Acetone conversion (%) | 79.5 | 66.0 | 85.2 | 79.9 | 81.2 | 88.7 | 76.3 |
| 4,4'-BPA Selectivity (%) | 92.4 | 91.7 | 94.3 | 94.6 | 92.8 | 94.4 | 94.5 |

TABLE 3

| | Example | | | Comparative Example | |
|---|---|---|---|---|---|
| | 11 | 12 | 13 | 8 | 9 |
| m (Formula 2) | 4 | 5 | 4 | 6 | (Formula 5) |
| a (Formula 2) | 2 | 2 | 3 | 2 | (Formula 5) |
| b (Formula 2) | 0 | 0 | 0 | 0 | (Formula 5) |
| $R^1$ (Formula 2) | H | H | H | H | (Formula 5) |
| % Modification (%) | 22.0 | 16.5 | 20.9 | 19.0 | 20.0 |
| % Residual sulfonic acid (%) After 40 hours | 78.0 | 83.2 | 78.8 | 81.0 | 80.0 |
| Acetone conversion (%) | 92.6 | 92.1 | 93.3 | 85.8 | 86.1 |
| 4,4'-BPA Selectivity (%) | 92.4 | 93.9 | 93.5 | 92.0 | 94.1 |

TABLE 3-continued

|  | Example | | | Comparative Example | |
|---|---|---|---|---|---|
|  | 11 | 12 | 13 | 8 | 9 |
| After 300 hours | | | | | |
| Acetone conversion (%) | 93.1 | 91.8 | 93.5 | 85.0 | 85.2 |
| 4,4'-BPA Selectivity (%) | 92.5 | 92.2 | 92.8 | 92.5 | 94.4 |

TABLE 4

|  | Example | | | | | | |
|---|---|---|---|---|---|---|---|
|  | 14 | 15 | 16 | 17 | 18 | 19 | 20 |
| a (Formula 1) | 2 | 2 | 3 | 3 | 3 | 3 | 2 |
| b (Formula 1) | 0 | 0 | 0 | 0 | 0 | 0 | 0 |
| $R^1$ (Formula 1) | H | H | H | H | H | H | H |
| $R^2$ (Formula 1) | Me | Me | Me | n-Bu | n-Bu | n-Bu | Me |
| $R^3$ (Formula 1) | Me | Me | Me | n-Bu | n-Bu | n-Bu | Me |
| % Modification (%) | 12.9 | 22.7 | 14.5 | 13.0 | 19.1 | 16.0 | 12.5 |
| % Residual sulfonic acid (%) | 87.0 | 77.2 | 85.0 | 86.5 | 80.3 | 83.6 | 87.5 |
| LHSV (hr$^{-1}$) | 1.0 | 1.0 | 1.0 | 1.0 | 1.0 | 0.6 | 1.0 |
| After 40 hours | | | | | | | |
| Acetone conversion (%) | 94.2 | 96.0 | 94.0 | 92.8 | 95.5 | 99.2 | 90.4 |
| 4,4'-BPA Selectivity (%) | 94.2 | 95.0 | 94.9 | 94.8 | 95.4 | 95.3 | 94.1 |
| After 300 hours | | | | | | | |
| Acetone conversion (%) | 93.4 | 96.0 | 94.7 | 92.6 | 96.0 | 99.3 | 89.9 |
| 4,4'-BPA Selectivity (%) | 94.5 | 94.7 | 94.8 | 95.7 | 95.2 | 95.4 | 94.2 |

TABLE 5

|  | Reference Example | | |
|---|---|---|---|
|  | 1 | 2 | 3 |
| a (Formula 1) | 1 | 2 | 3 |
| b (Formula 1) | 0 | 0 | 0 |
| $R^1$ (Formula 1) | H | H | H |
| $R^2$ (Formula 1) | H | Me | n-Bu |
| $R^3$ (Formula 1) | H | Me | n-Bu |
| % Modification (%) | 15.0 | 15.0 | 15.0 |
| % Residual sulfonic acid (%) | 85.0 | 84.9 | 84.8 |
| No addition of water | | | |
| Acetone conversion (%) | 65.8 | 78.3 | 100 |
| Addition of water | | | |
| Acetone conversion (%) | 21.1 | 45.5 | 89.2 |

What is claimed is:

1. In a process for preparing a bisphenol by the catalytic condensation reaction of a phenol with a ketone, the improvement which comprises the use of a catalyst which is a modified ion exchange resin comprising a strongly acidic ion exchange resin of a sulfonic acid type having an N,N-di-substituted mercaptoalkylamine ionically bound thereto, the N,N-di-substituted mercaptoalkylamine being represented by the formula (0):

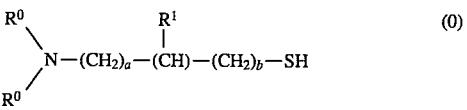

wherein $R^1$ represents hydrogen or an alkyl group having 1–6 carbon atoms, and $R^0$s independently represent an alkyl group having 1–10 carbon atoms or the substituents $R^0$ are bonded to each other at their ω-terminals to form an alkylene ring having 4–5 carbon atoms together with the nitrogen atom, a and b independently denote an integer from 0 to 3, and a+b equals 2 or 3.

2. The process for preparing a bisphenol according to claim 1, wherein the N,N-di-substituted mercaptoalkylamine is represented by the formula (1):

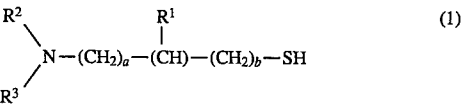

wherein $R^2$ and $R^3$ independently represent an alkyl group having 1–10 carbon atoms, and $R^1$, a and b have the same meanings as defined for the formula (0).

3. The process for preparing a bisphenol according to claim 1, wherein the N, N-di-substituted mercaptoalkylamine is represented by the formula (2):

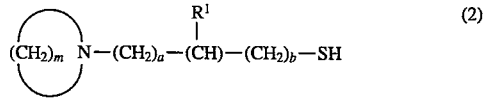

wherein m denotes an integer of 4 or 5, and $R^1$, a and b have the same meanings as defined for the formula (0).

4. A process for preparing a bisphenol according to claim 1, wherein the amount of the N,N-di-substituted mercaptoalkytamine ionically bound is in 3–40% of the sulfonic acid group.

5. A process for preparing a bisphenol according to claim 1, wherein the phenol is an unsubstituted phenol and the ketone is acetone, and the bisphenol to be produced is bisphenol A.

6. A process for preparing a bisphenol according to claim 1, wherein the strongly acidic ion exchange resin of a sulfonic acid type comprises a sulfonated product of a styrene-divinyl benzene copolymer.

7. The process for preparing a bisphenol according to claim 1, wherein $R^1$ represents hydrogen or an alkyl group having 1–4 carbon atoms, and $R^0$s independently represent an alkyl group having 1–6 carbon atoms.

8. The process for preparing a bisphenol according to claim 2, wherein $R^1$ represents hydrogen or an alkyl group having 1–4 carbon atoms, and $R^2$ and $R^3$ independently represent an alkyl group having 1–6 carbon atoms.

* * * * *